United States Patent
Rohlfing et al.

(10) Patent No.: US 11,116,559 B2
(45) Date of Patent: Sep. 14, 2021

(54) SURGICAL INSTRUMENT AND METHOD

(71) Applicant: Warsaw Orthopedic, Inc., Warsaw, IN (US)

(72) Inventors: Alexander J. Rohlfing, Memphis, TN (US); Jason M. May, Collierville, TN (US); Dustin Bobbitt, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 280 days.

(21) Appl. No.: 15/899,081

(22) Filed: Feb. 19, 2018

(65) Prior Publication Data

US 2019/0254730 A1 Aug. 22, 2019

(51) Int. Cl.
 *A61B 17/88* (2006.01)
 *A61B 17/70* (2006.01)

(52) U.S. Cl.
 CPC ...... *A61B 17/8888* (2013.01); *A61B 17/7082* (2013.01); *A61B 17/8891* (2013.01)

(58) Field of Classification Search
 CPC .......................... A61B 17/8888; A61B 17/8891
 See application file for complete search history.

(56) References Cited

U.S. PATENT DOCUMENTS

| | | | | |
|---|---|---|---|---|
| 1,874,657 A | * | 8/1932 | Trotter | F16B 35/005 411/306 |
| 4,763,548 A | * | 8/1988 | Leibinger | A61B 17/8891 81/438 |
| 5,291,811 A | | 3/1994 | Goss | |
| 5,605,080 A | * | 2/1997 | Pfefferle | A61B 17/8891 81/438 |
| 5,649,931 A | * | 7/1997 | Bryant | A61B 17/8891 606/104 |
| 6,827,822 B2 | | 12/2004 | Tao et al. | |
| 6,955,678 B2 | | 10/2005 | Gabriel et al. | |
| 6,997,086 B1 | | 2/2006 | Graham | |
| 7,137,985 B2 | | 11/2006 | Jahng | |
| 7,717,921 B2 | | 5/2010 | Rezach | |
| 8,075,579 B2 | | 12/2011 | Hamada | |
| 8,105,328 B2 | | 1/2012 | Protopsaltis | |
| 8,636,778 B2 | | 1/2014 | Gephart et al. | |

(Continued)

OTHER PUBLICATIONS

International Search Report and Written Opinion for PCT/US2019/017955 the counterpart application dated May 23, 2019, 24 pages.

*Primary Examiner* — Nicholas W Woodall
(74) *Attorney, Agent, or Firm* — Sorell, Lenna & Schmidt, LLP

(57) ABSTRACT

A surgical instrument includes a first member that includes a first element engageable with an inner surface of a head of a bone fastener and a second element engageable with an outer surface of the head. The first member defines a first-member longitudinal axis and the bone fastener defines a bone-fastener longitudinal axis. A second member defines a second-member longitudinal axis and is movable relative to the first member and engageable with the second element to dispose the first element and the second element with the head in a co-axial, capture orientation. wherein the first-member, bone-fastener, and second-member longitudinal axes are aligned. Systems, spinal constructs, implants and methods are disclosed.

20 Claims, 12 Drawing Sheets

(56) References Cited

U.S. PATENT DOCUMENTS

| | | | |
|---|---|---|---|
| 10,105,165 B2* | 10/2018 | Biedermann | A61B 17/7082 |
| 2004/0215190 A1* | 10/2004 | Nguyen | A61B 17/1671 |
| | | | 606/86 A |
| 2004/0243139 A1 | 12/2004 | Lewis et al. | |
| 2006/0111713 A1 | 5/2006 | Jackson | |
| 2007/0043378 A1* | 2/2007 | Kumar | A61B 17/7082 |
| | | | 606/104 |
| 2011/0046683 A1* | 2/2011 | Biedermann | A61B 17/7035 |
| | | | 606/305 |
| 2012/0290016 A1 | 11/2012 | Kumar | |
| 2013/0274814 A1* | 10/2013 | Weiner | A61B 17/8883 |
| | | | 606/301 |
| 2013/0310842 A1 | 11/2013 | Winkler et al. | |
| 2014/0031872 A1 | 1/2014 | Jackson | |
| 2014/0276892 A1 | 9/2014 | Pakzaban et al. | |
| 2014/0324062 A1* | 10/2014 | Heuer | A61B 17/7082 |
| | | | 606/104 |
| 2015/0257797 A1* | 9/2015 | Biedermann | A61B 17/7082 |
| | | | 606/305 |
| 2016/0151101 A1* | 6/2016 | Machida | A61B 17/864 |
| | | | 606/308 |
| 2016/0324552 A1* | 11/2016 | Baker | A61B 17/1728 |
| 2016/0338742 A1 | 11/2016 | Peterson et al. | |

\* cited by examiner

SURGICAL INSTRUMENT AND METHOD

TECHNICAL FIELD

The present disclosure generally relates to medical devices for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, scoliosis, kyphosis and other curvature abnormalities, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, which include implants such as bone fasteners, connectors, plates and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attachment to the exterior of two or more vertebral members. This disclosure describes an improvement over these prior technologies.

SUMMARY

In one embodiment, a surgical instrument is provided. The surgical instrument includes a first member that includes a first element engageable with an inner surface of a head of a bone fastener and a second element engageable with an outer surface of the head. The first member defines a first-member longitudinal axis and the bone fastener defines a bone-fastener longitudinal axis. A second member defines a second-member longitudinal axis and is movable relative to the first member and engageable with the second element to dispose the first element and the second element with the head in a co-axial, capture orientation, wherein the first-member, bone-fastener, and second-member longitudinal axes are aligned. In some embodiments, systems, spinal constructs, implants and methods are disclosed.

In one embodiment, the surgical method includes the steps of: engaging an inner drive with an inner surface of a head of a bone fastener, yielding a first engagement; engaging an outer surface of the head with an inner portion of an outer tube, surrounding the inner drive, yielding a second engagement; and driving the bone fastener into patient tissue by force applied to the fastener via the inner drive, with alignment between longitudinal axes of the inner drive, the bone fastener, and the outer tube being maintained based on the first and second engagements.

In one embodiment, the surgical instrument includes an inner drive engageable with an inner surface of a head of a bone fastener. The inner drive defines an inner-drive longitudinal axis and the bone fastener defines a bone-fastener longitudinal axis. An outer sleeve has an outer-sleeve axis and includes a threaded surface engageable with a threaded portion of an outer surface of the head to dispose the inner drive and the outer sleeve with the head in a co-axial, capture orientation, wherein the inner-drive longitudinal axes, the bone-fastener longitudinal axis, and the outer-sleeve axis are aligned.

BRIEF DESCRIPTION OF THE DRAWINGS

The present disclosure will become more readily apparent from the specific description accompanied by the following drawings, in which.

DETAILED DESCRIPTION

Figure 1:
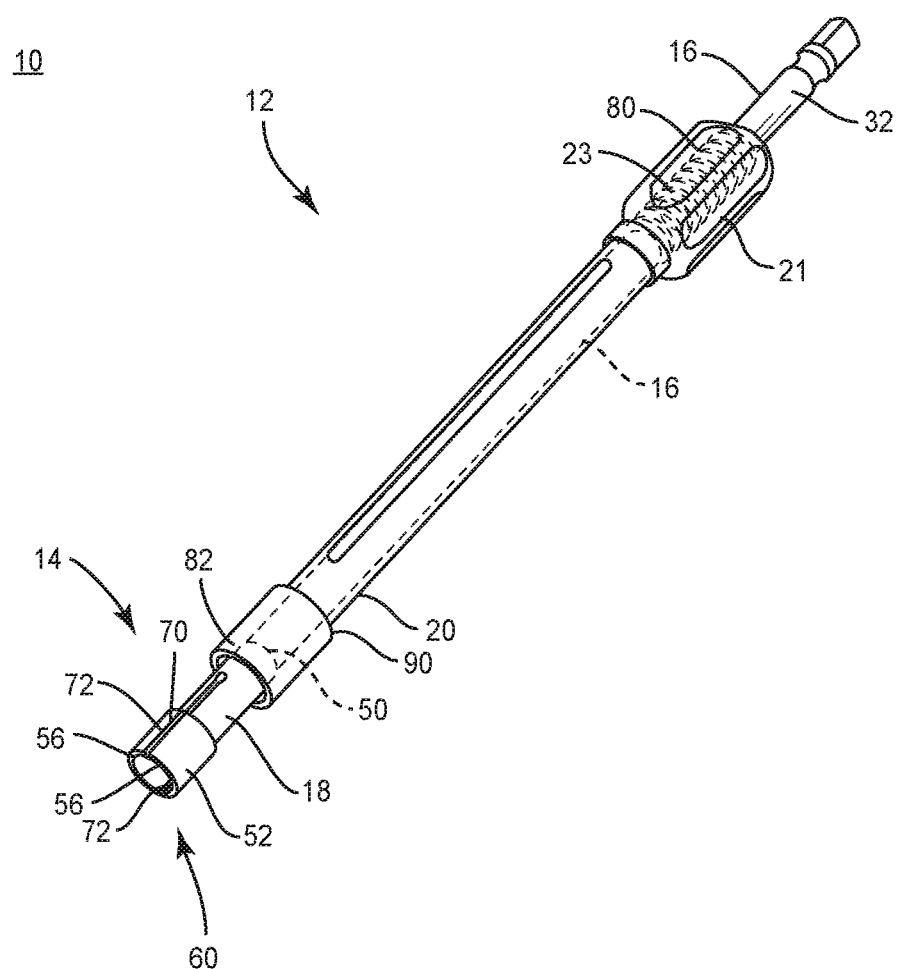
FIG. 1 is a perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system and a method for treating a spine. In some embodiments, the present surgical system comprises a surgical instrument, such as, for example, a driver engageable with a screw shank. In some embodiments, the present surgical system comprises a surgical instrument, such as, for example, a driver engageable with a screw via a drive interface.

In some embodiments, the present surgical system comprises a surgical instrument, such as, for example, a collet shank driver. In some embodiments, the present surgical system comprises a driver configured for use with a modular screw platform. In some embodiments, the driver is configured for engagement with a screw shank, without a tulip head attached, and maintains the driver and the shank in a rigid coaxial connection. In some embodiments, the driver is configured with an increased torque capacities compared to conventional drivers. In various embodiments, the driver instrument and bone fastener of the present technology are configured to have a higher torque capacity as compared to conventional driver/fastener arrangements.

In some embodiments, the driver includes a collet and a sleeve. In some embodiments, the sleeve is sized to grasp a spherical head of the screw shank. In some embodiments, the sleeve is configured to collapse and apply a force about the collet to close the collet. In some embodiments, the screw shank is axially translated into the driver. As the screw shank translates, the screw head is compressed. Compression of the screw head causes the screw head to deform such that there is a rigid, or more rigid, coaxial connection.

In some embodiments, the driver includes a drive geometry configured for increased performance in a cannulated driver configuration. In some embodiments, the driver includes laser marked regions to be used in connection with uni-axial features of the bone fastener. A uni-axial bone fastener typically has opposing flats, or flat portions (not shown in detail), on its head, allowing a user to grasp the head on the flats for robust holding while also allowing the fastener to be rotated in one direction—i.e., about one (uni) axis. The rotation is generally about the grasp points, on the flats. Driver marking(s) can indicate, for instance, a circumferential positioning that the surgical system should have with respect to a uni-axial bone fastener. A user can use them to align the surgical system with the fastener as desired to ensure that the fastener can subsequently be moved in the uni-axial direction while being held.

In some embodiments, the driver includes a triple lead to provide for an increased translation of the sleeve with fewer rotations. In some embodiments, the drive geometry includes lobes shaped by elliptical cuts. In some embodiments, the lobes are configured with an increased surface contact area between male and female drive geometries to distribute stresses throughout an increased portion of the lobes, increasing the torque-to-failure ratio as compared to conventional drive systems.

In some embodiments, the surgical instrument comprises a driver having a two-piece design. In some embodiments, the driver is compatible with an actuator, such as, for example, a powered surgical drill. In some embodiments, the sleeve includes a stop element configured to facilitate depth control. In some embodiments, the driver includes a collet and a sleeve configured to tighten the collet about the screw shank.

In some embodiments, the surgical system is utilized with a method including the step of disposing a driver in an initial open configuration by translating the sleeve out of engagement with the collet allowing the collet to expand for disposal of the screw shank. In some embodiments, the method includes the step of inserting the screw shank into the collet. In some embodiments, the method includes the step of aligning flats of the screw shank with a laser marking to engage the male and female features of the drive geometries and/or for indexing drive geometry. In some embodiments, the method includes the step of translating the sleeve into engagement with the collet such that the collet compresses the screw shank and draws the screw shank into engagement with the driver geometry. In some embodiments, the method includes the step of drawing the screw shank into the collet to cause the driver to apply a force to the screw shank creating a rigid, coaxial connection. In some embodiments, the method includes the step of engaging the screw shank with tissue. In some embodiments, the method includes the step of translating the sleeve out of engagement with the collet to release the screw shank.

In some embodiments, the present surgical system can serve functions performed conventionally by multiple surgical instruments. For this reason, instruments according to the present technology can be said to provide for consolidation of a driver portfolio. As an example, some conventional driver portfolios included multiple instruments to accommodate various types of bone fastener head formations, such as fixed heads and various types of multi-axial heads (e.g., tulip heads), such as those including any of various types of reducers for rod insertion, and various types of multi-axial heads that do not include a reducer.

With the present technology, a single bone-fastener can be inserted, and then, subsequently, converted as desired by addition of another head component. A fastener according to the present technology can be inserted using the surgical instrument disclosed, for instance, and then a first tulip head, having a reduction feature, can be added to the fastener inserted. Alternatively, the same fastener can be inserted, and a second tulip head, having a different, or no, reduction feature, can be added to the fastener instead. Thus, the same driver instrument can be used to drive in a fastener flexible to operate as any of various types of bases for other structural (e.g., rods, plates) components. Prior, various drivers were needed to insert screws of such various configurations into patients.

Driver portfolios can also be consolidated, or simplified, by embodiments of the present technology providing a novel cannulated driver. The new driver, in connection with the newly configured bone fastener head of the present technology, is, in cannulated and non-cannulated embodiments, stronger than prior systems. The fully cannulated versions of the present technology (cannulated drive and fastener), for instance, allow creation of more torque than not only prior cannulated drivers and/or fasteners, but also prior solid drivers and fasteners. A physician can thus use the cannulated drives according to the present technology in place of multiple drivers that were used before under various conditions, such as some conditions requiring cannulation of the driver and/or fastener, and some requiring greater torque application, for which solid components had to be used.

In some embodiments, the drive geometry includes elliptical shaped lobes. In some embodiments, the lobes include a minor diameter configured to increase torque capacity.

Figure 19:
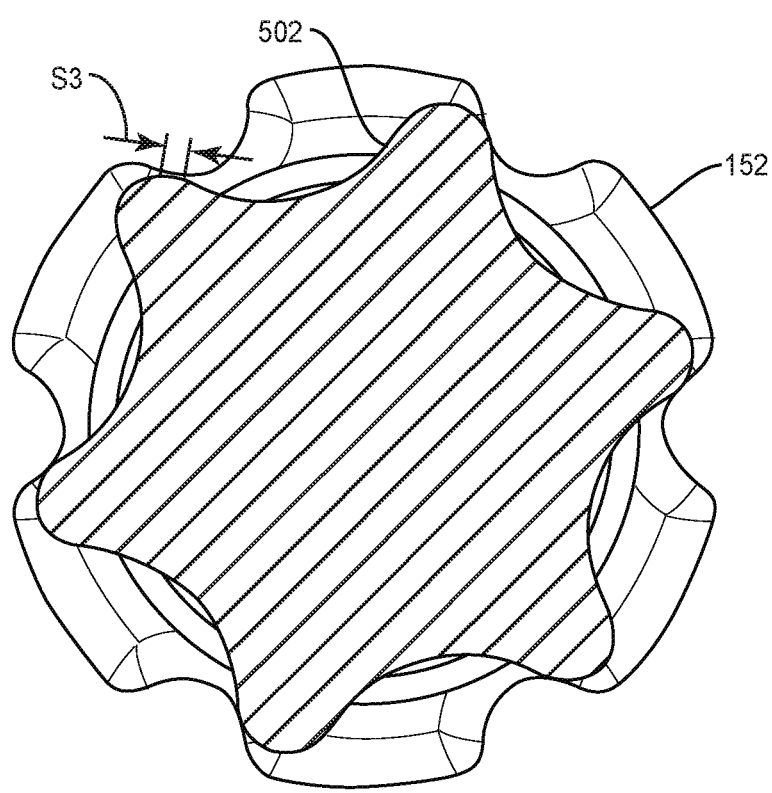
FIG. 19 shows interfacing engagement portions of a conventional surgical instrument and a surgical bone fastener according to the present technology.

In some embodiments, the present surgical system includes a bone fastener having a female socket compatible with a standard T25 drive. A benefit of using the bone fastener of the present technology is that, if needed, a conventional (e.g., T25) driver can be used with it, such as to remove the fastener from the patient. This functional mismatch of components may be occasioned if, for instance, a first physician used the new driver to install the new bone fastener and, subsequently, the same or another physician, who does not have the new driver, wants to remove the fastener. An example interface between a conventional, T25, driver with the new bone fastener of the present technology is shown in FIG. 19.

In some embodiments, the drive geometry includes elliptical shaped lobes having edges of elliptical cuts that create an increase in surface area between contact surfaces resulting in an increased torque capacity as compared to conventional drive systems. In some embodiments, the lobes create more surface-to-surface contact where force is applied from the driver to the bone fastener, as compared to prior systems, such as a standard T25 driver to a T25 screw, which create more of a point contact, or contact generally along a line. The increased surface-to-surface contact distributes stress to the lobe more efficiently than such standard drives.

In some embodiments, each lobe includes an increased cross-sectional area as compared to protrusions of prior interfaces, such as of T25 arrangements, which is configured to increase torque capacity. In some embodiments, the lobe is configured to provide for an increased distribution of stress from a tip of the lobe.

It is contemplated that the arrangement of the present arrangement may be stronger, allowing for creation of greater torque without instrument or fastener failure, because of configuration, other than the elliptical radius features, compared to the same of protrusions of conventional drivers and fasteners. It is contemplated, for instance, that the arrangement of the present arrangement may be stronger, allowing for creation of greater torque without instrument or fastener failure, because the lobes of the driver and/or of the fastener are shorter, or lower, than the protrusions of conventional drivers and fasteners, such as the T25 arrangement. It is also contemplated that the arrangement of the present arrangement may be stronger, allowing for creation of greater torque without instrument or fastener failure, because the lobes of the driver and/or of the fastener have a relatively wider profile compared to a width of protrusions of conventional drivers and fasteners. These structures and benefits are described further below with reference to the drawings.

In some embodiments, the surgical instrument comprises a driver configured to be utilized with multiple design requirements of a modular screw platform. In some embodiments, the surgical instrument includes a driver configured to drive a bone screw shank without a tulip head attached thereto. In some embodiments, the present surgical system is configured to provide a rigid, coaxial connection between the driver and the shank. In some embodiments, the present surgical system includes a threaded connection between the surgical instrument and the bone screw shank to form a rigid, co-axial connection and decrease toggle between components. In some embodiments, the driver includes an M7×0.5 thread disposed with an upper portion of the screw shank. In some embodiments, the thread provides an interface between the shank and the driver. In some embodiments, the driver includes a mating M7 thread. In some embodiments, the thread on the screw shank can be utilized as an interface with other instruments and implants, such as, for example, retractors, compressors/distractors, and screw head attachments.

In some embodiments, the surgical instrument comprises an M7 threaded driver. In some embodiments, the surgical instrument includes an outer sleeve engageable with the screw shank via an external thread on a sphere of the screw shank to create a rigid, coaxial connection. In some embodiments, the surgical instrument includes a three-piece design that is configured to be fully disassembled to allow for cleaning and/or sterilization. In some embodiments, the surgical instrument is configured for connection with a powered surgical drill and/or a nerve monitoring system. In some embodiments, the present surgical system includes a M7×0.5 thread incorporated into a driver sleeve and a screw shank. In some embodiments, the surgical instrument includes an increased outer diameter of the driver shaft to provide more surface-to-surface contact to index, or better index, the driver to the screw shank, as compared to prior systems, such as a standard T25 driver to T25 screw.

In some embodiments, the surgical instrument includes an outer sleeve having thread runout dimensioning to ensure a rigid connection with approximately two full revolutions of the outer sleeve. In some embodiments, the surgical instrument includes a depth stop element configured to resist and/or prevent driving the screw shank beyond a selected limit, ensuring enough space for a snap-fit or pop-on head attachment. In some embodiments, the surgical instrument includes a drive having a flanged feature configured to engage the sleeve and causes the interface connection of the surgical instrument and the bone screw shank to lock up before thread runout on the shank. In some embodiments, the surgical instrument includes a cavity disposed with the sleeve that is configured to allow for translation of the drive shaft such that the drive protrudes from the sleeve to facilitate mating of the drive geometries before threading the screw shank with the sleeve. In some embodiments, the flanged feature provides for connection of the drive with the screw shank with threads fully engaged.

In some embodiments, the surgical instrument comprises a threaded driver employed with a method including the step of disposing the driver in an initial open orientation such that the driver shaft extends from a sleeve of the surgical instrument. In some embodiments, the method includes the step of engaging the screw shank drive geometry with the drive geometry of the driver. In some embodiments, the method includes the step of positioning the screw shank with the sleeve such that the screw shank thread contacts the inside of the sleeve. In some embodiments, the method includes the step of threading the sleeve with the screw shank. In some embodiments, the method includes the step of translating the drive shaft such that a flange contacts a sleeve cap causing a threaded connection to lock up before the threads run out. In some embodiments, the method includes the step of rotating the sleeve counterclockwise to disengage from the screw shank. In some embodiments, the method includes the step of detaching the driver from the screw shank.

In some embodiments, the present surgical system is configured for connection with various instruments utilizing the threaded connection, such as, for example, retractors, compressors and/or distractors. In some embodiments, the threaded connection can be utilized for engagement with other implants. In some embodiments, the surgical instrument includes a thread runout dimensioned so that it will not interfere with head angulation of a bone screw.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or anterolateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing implanting instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-4, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyactide, polyglycolide, polytyrosine carbonate, polycaroplaetohe and their combinations.

The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 can be employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of surgical system 10 are configured for engagement with existing spinal constructs, which may include spinal implants such as one or more rods, fasteners, plates and connectors. In some embodiments, the spinal constructs can be attached with vertebrae in a revision surgery to manipulate tissue and/or correct a spinal disorder, as described herein.

Surgical system 10 includes a surgical instrument 12. In some embodiments, surgical instrument 12 is configured for use with a bone fastener 150, as shown for example in FIG. 2. Surgical instrument 12 includes a member, such as, for example, an inner sleeve 14. Inner sleeve 14 includes an element, such as, for example, an inner drive 16 engageable with a head 152 (FIG. 2 and FIGS. 4-9) of bone fastener 150, and an element, such as, for example, an outer tube 18 engageable with an outer surface 156 of head 152. A member, such as, for example, an outer sleeve 20 is movable relative to inner sleeve 14 and engageable with tube 18 to dispose inner drive 16 and tube 18 with head 152 in a co-axial, capture orientation to facilitate accurate engagement of bone fastener 150 with tissue. Sleeve 20 is configured to compress a portion of tube 18, for example, a lower portion, shown in FIG. 2, to form a rigid connection between surgical instrument 12 and bone fastener 150 to maintain the co-axial orientation.

Figure 2:
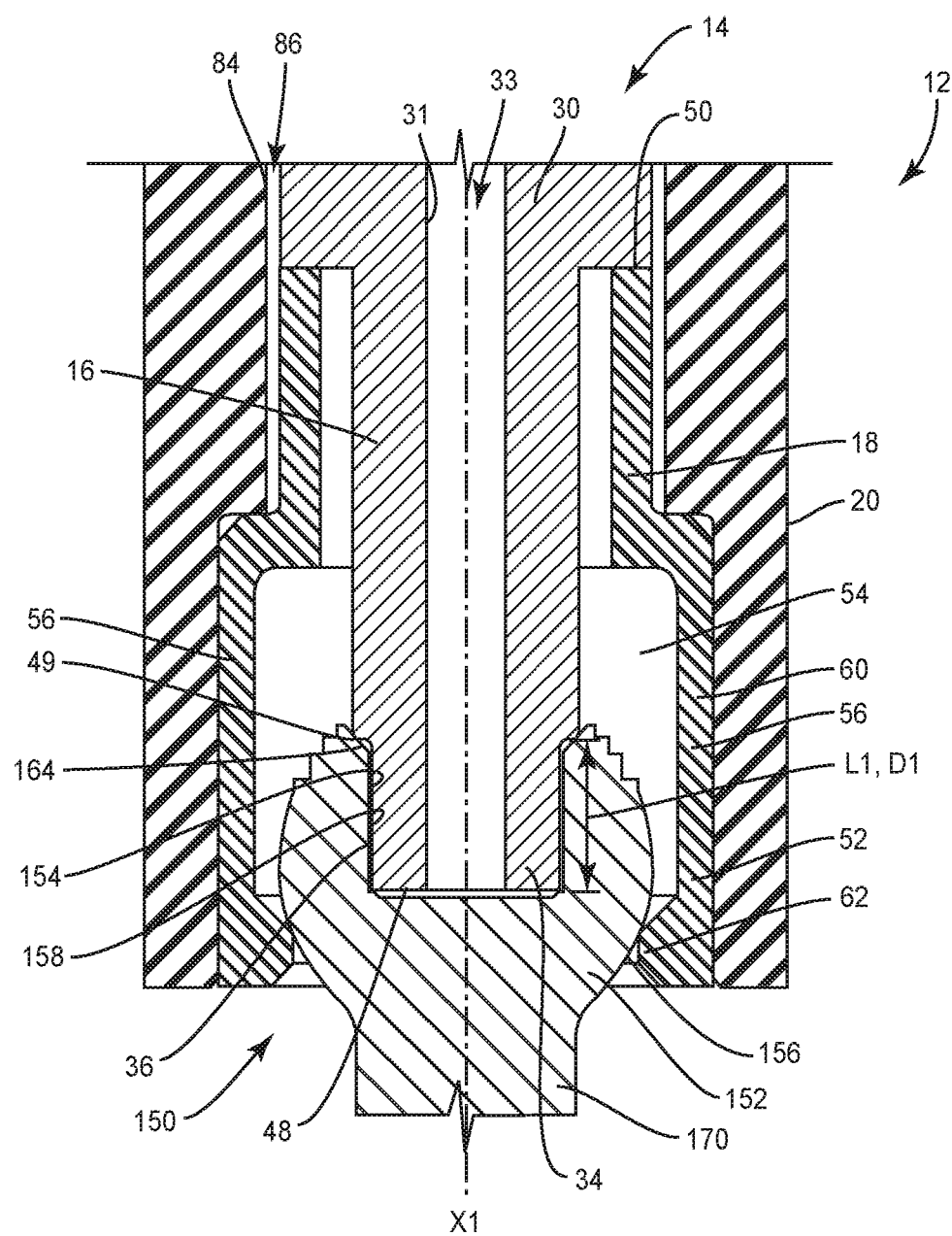
FIG. 2 is an enlarged cross section view of components of one embodiment of a surgical system in accordance with the principles of the present disclosure.

Drive 16 includes a shaft 30 that extends between an end 32 (FIG. 1) and an end 34 (FIG. 2). Drive 16 extends along an axis X1. In some embodiments, end 32 includes a hexagonal geometry configured for engagement with a similarly shaped surgical tool, such as, for example, a portion of a driver (not shown). Shaft 30 includes a surface 31 that defines a passageway 33 such that shaft 30 includes a cannulated configuration. End 34 includes a drive interface, such as, for example, an engagement portion 36 configured to mate with a socket 158 of head 152, as shown in FIG. 2.

Engagement portion 36 includes an outer surface 38 defining an element, such as, for example, a lobe 40. In some embodiments, engagement portion 36 includes one or a plurality of elements. In some embodiments, engagement portion 36 includes six (6) lobes 40. Engagement portion 36 includes a plurality of spaced apart lobes 40 disposed circumferentially about engagement portion 36. Lobes 40 are spaced apart by grooves 37, as shown in FIG. 3.

Figure 3:
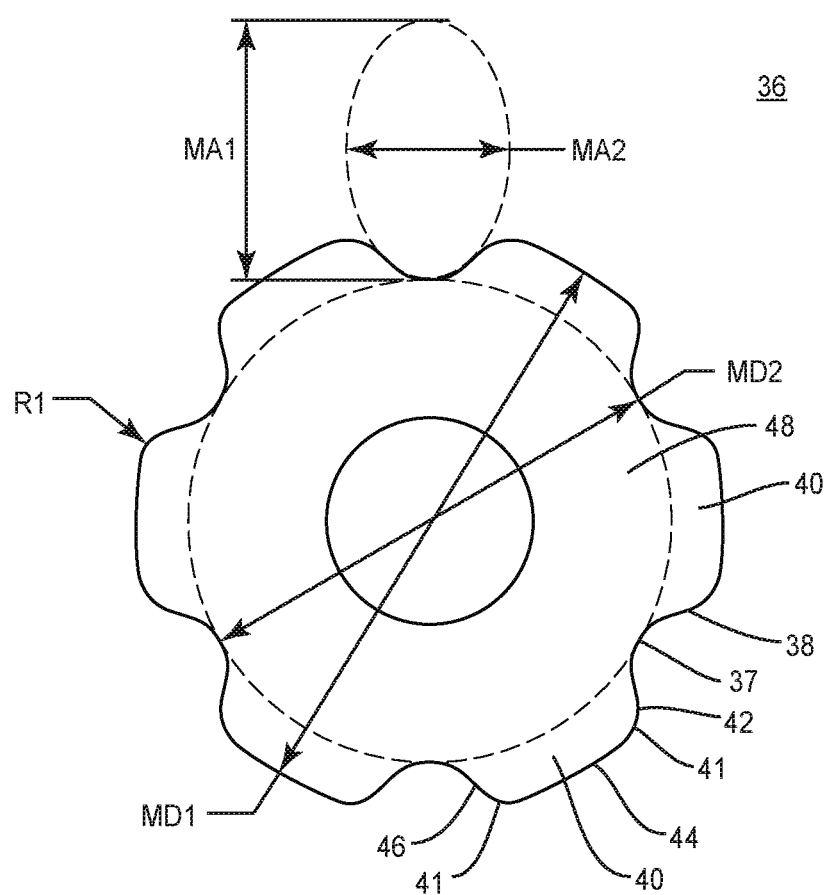
FIG. 3 is an end view of components of one embodiment of a surgical system in accordance with the principles of the present disclosure.

In various embodiments, a shape of each lobe 40 is fully or at least partially defined by dimensions of a pre-established ellipse having a major axis MA1 and a minor axis MA2, as shown in FIG. 3. In various embodiments, each lobe 40 includes an elliptical drive edge 42, a tip edge 44 and an elliptical trailing edge 46. The drive and trailing edges are referred to as elliptical because their shape is defined at least partially by the ellipse. The major and minor axis are the same, or almost or generally the same, in which case the shape is thus circular or nearly so. And the elliptical edges can be referred to as circular edges.

Edge 42 is engageable with a surface of head 152 to apply a torque to drive and/or rotate bone fastener 150, as described herein. In some embodiments, lobes 40 are configured to transmit and/or withstand a higher, or much higher, torque as compared with conventional drive systems.

In various embodiments, the surgical systems 10 of the present technology can be used to create between 25-35% more torque than a conventional system, such as a system having a conventional T25 driver and a T25-headed bone fastener. In some embodiments, the new driver and fastener create about 30% more torque. The new system, in various embodiments, can create a torque of between about 17 nm to about 25 Nm for instance, versus about 10 Nm to about 12 Nm that can be generated by a conventional cannulated driver, before the cannulated driver breaks, and versus about 16 Nm that can be generated by a conventional T25 non-cannulated driver, before the non-cannulated driver breaks. In a particular embodiment, the new system allows a user to generate between about 18 Nm and about 23 Nm, and in some embodiments, allows generation of about 18, 19, 20, 21, 22, or 23 Nm.

In various embodiments, the major elliptical axis MA1 is between about 1.0 mm and about 2.5 mm. In some embodiments, the major diameter MA1 is between about 1.5 mm and about 2.0 mm, and in particular embodiments, is about 1.5, 1.6, 1.7, 1.8, 1.9, or 2.0 mm. In various embodiments, the minor diameter MA2 is between about 1.0 mm and about 2.5 mm. In some embodiments, the major diameter MA2 is between about 1.5 mm and about 2.0 mm, and in particular embodiments, is about 1.5, 1.6, 1.7, 1.8, 1.9, or 2.0 mm.

The configuration of lobe 40 provides an increased surface contact area between a surface of head 152 and lobe 40. Lobe 40 is configured to better distribute the stresses applied by the act of driving the bone fastener 150 with the drive 16, as compared to prior systems, such as those using a standard T25 driver and T25 fastener head. Lobes 40 are sized and shaped to establish more surface-to-surface contact between the driver and fastener head than is established with the conventional arrangements, for example, and thereby to distribute the driving forces or stresses better, throughout lobes 40, as compared to the more concentrated force/stress distribution created in the conventional arrangements.

Figure 18:
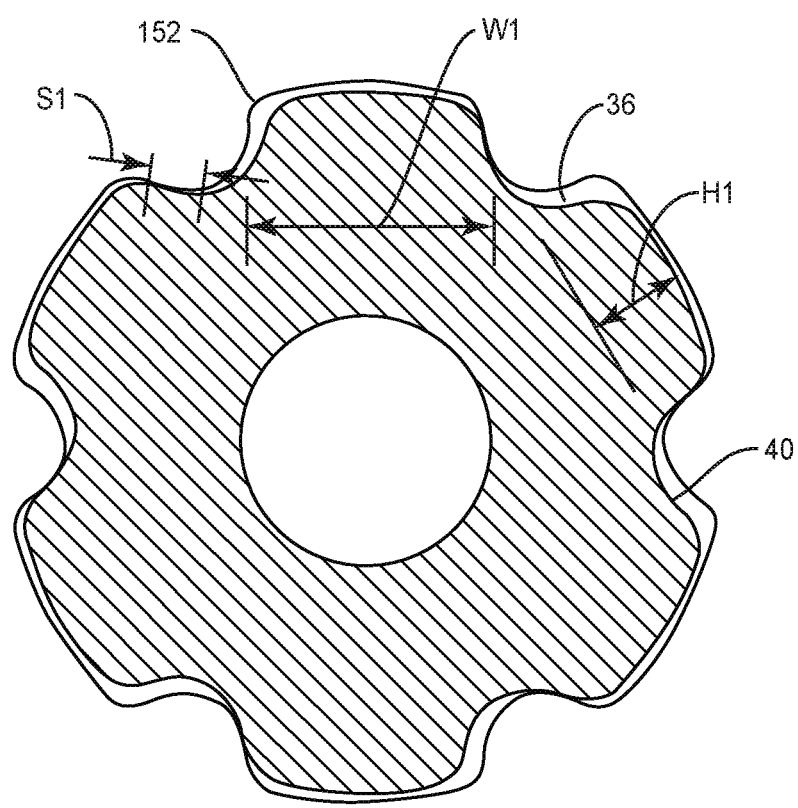
FIG. 18 shows interfacing engagement portions of a surgical instrument and a surgical bone fastener of the surgical systems of FIGS. 1-17.

With reference to FIG. 18, S1 indicates the increased surface-to-surface contact between the engagement portion 36/236 (FIGS. 1 and 11) of the drivers 16/216 of the present technology and the engagement portion 154/354 (FIGS. 1 and 11) of the bone fastener. Conventional drivers have a lower surface-to-surface contact between the engagement portion of a T25 driver and an engagement portion of a T25 fastener head.

As mentioned, in some embodiments, the present bone fasteners 150 (and 350) include a female socket 158 compatible with conventional drivers, such as a standard T25 driver. A benefit of using the bone fastener of the present technology is thus that, if needed, a conventional (e.g., T25) driver can be used with it, such as to remove the fastener from the patient. An example interface between a conventional, T25, driver with the new bone fastener of the present technology is shown in FIG. 19.

In embodiments in which a conventional, e.g., T25, driver is used with a bone fastener of the present technology, less surface-to-surface contact is created as compared to the surface-to-surface contact, indicated by S1 in FIG. 18, between the driver of the present technology and the fastener of the present technology.

In embodiments in which a conventional, e.g., T25, driver is used with a bone fastener of the present technology, less surface-to-surface contact, indicated by section S3 in FIG. 19, is created as compared to the surface-to-surface contact, indicated by S1 in FIG. 18, between the driver of the present technology and the fastener of the present technology.

As mentioned, the present arrangement is stronger, allowing for creation of greater torque without instrument or fastener failure, based on the elliptical-based features. The arrangement can also be stronger due to other aspects of driver and/or fastener configuration.

It is contemplated that the arrangement of the present arrangement can be stronger, for example, because the lobes of the driver and/or of the fastener have a relatively lower profile. As an example, a first lobe height H1, shown in FIG. 18, is lower than a height of protrusions of conventional drivers and fasteners, such as of a T25 arrangement.

And in some embodiments, the arrangement of the present arrangement is stronger, allowing for creation of greater torque without instrument or fastener failure, because the lobes of the driver and/or of the fastener have a relatively wider profile. As an example, a first width W1, in FIG. 18, of the lobes 40, of the present technology, is larger than a width of protrusions of an example conventional driver, such as the T25 arrangement.

With continued reference to FIG. 2, in various embodiments, each lobe 40 extends along a length L1 of the driver, in the axial direction. Each lobe 40 includes two transition portions 41 between or joining its tip edge 44 and the adjacent drive and trailing edges 42, 44. In various embodiments, at least one of the transition portions 41 is curved, having a radius of curvature R1. In various embodiments, radius R1 is between about 0.2 mm and about 0.4 mm. In some embodiments, radius R1 is about 0.2, 0.3, or 0.4 mm. In a contemplated embodiment (not shown in detail), at least one of the transition portions 41 includes a corner instead of a rounded radius. The corner can have an internal angle between about 30 degrees and about 60 degrees, as an example.

Edges 42, 46 extend along length L1. In some embodiments, edge 42 and/or edge 46 include a linear configuration. In some embodiments, all or portions of edge 42 and/or edge 46 may include various configurations and/or be disposed in various orientations, such as, for example, angular, arcuate, undulating, series, parallel, offset and/or staggered. Extension of edge 42 along length L1 disposes an entirety of, or substantially all, of a surface of edge 42 into contacting engagement with an interface surface of the surface that defines a socket of bone fastener 150, as described herein, causing an increase in torque capacity as compared to a case in which edge 42 did not extend along the entire length L1. In some embodiments, such full contacting engagement, of all or substantially all, of the surface of edge 42 with the bone fastener 150, creates or at least facilitates a more rigid connection between surgical instrument 12 and bone fastener 150, as compared with conventional systems lacking the improvements described herein.

As mentioned, for example, edge 42 is configured, including based on the described elliptical shape, to more-uniformly and more-efficiently distribute load and stress throughout lobe 40, as compared to the force distributions of conventional systems.

Engagement portion 36 includes a distal face 48. Distal face 48, in various embodiments, includes a flat or even surface. In some embodiments, distal face 48 has one or more of various surface configurations, such as, for example, rough, threaded, arcuate, undulating, porous, semi-porous, dimpled, polished and/or textured. Distal face 48 includes a major diameter MD1 and a minor diameter MD2, as shown in FIG. 3.

In various embodiments, the major diameter MD1 is between about 4.0 mm and about 5.0 mm. In some embodiments, the major diameter MD1 is between about 4.3 mm and about 4.6 mm, and in particular embodiments, is about 4.3, 4.4, 4.5, or 4.6 mm.

In various embodiments, the minor diameter MD2 is between about 3.0 mm and about 5.0 mm. In some embodiments, the minor diameter MD2 is between about 3.0 mm and about 3.9 mm. In some embodiments, the minor diameter is between about 3.3 mm and about 3.6 mm, and in particular embodiments, is about 3.3, 3.4, 3.5, or 3.6 mm.

Engagement portion 36 of drive 16 may include a protrusion, such as, for example, a shoulder 49, as shown in FIG. 2. Shoulder 49 is circumferentially disposed about drive 16. Shoulder 49 is configured to engage a surface of head 152 to facilitate forming a rigid connection between surgical instrument 12 and bone fastener 150. For example, as bone fastener 150 is engaged with drive 16, shoulder 49 applies a force to a surface 164 of head 152 to deform and/or compress surface 164, such as where line 49 indicates in FIG. 2, to form, or at least as port of forming, the rigid connection between surgical instrument 12 and bone fastener 150.

In some embodiments, engagement portion 36 of drive 16 includes one or more locating indicia. In some embodiments, the indicia include a visual indicium, such as, a laser marking configured to facilitate indexing engagement portion 36 with socket 158. In some embodiments, the indicia may include any of visual indicia, tactile indicia, audible indicia, one or more components having markers for identification under x-ray, fluoroscopy, CT or other imaging techniques, a wireless component, a wired component, a near field communication component and/or one or more components that generate acoustic signals, magnetic signals, electromagnetic signals and/or radiologic signals. In some embodiments, the indicia includes a notch, slot, bead, detent, bump, print, label, score, color coding and/or cavity.

Tube 18 extends between an end 50 and an end 52. In some embodiments, tube 18 may have various cross-section configurations, such as, for example, oval, oblong, triangular, rectangular, square, polygonal, irregular, uniform, non-uniform, variable, tubular and/or tapered. End 50 includes a mating surface, such as, for example, an outer threaded surface (not shown) configured to facilitate translation of sleeve 20 relative to tube 18, as described herein.

End 52 is disposed in a spaced apart relation with end 34 of drive 16 to define a cavity 54, as shown in FIG. 2. Cavity 54 is configured for disposal of all or some of head 152. End 52 includes a plurality of radially moveable arms 56. Inner drive 16 and tube 18 define a collet 60, as shown in FIG. 1. Arms 56 radially move relative to drive 16. Arms 56 are disposable between an open orientation such that arms 56 are biased radially outwards, and a closed orientation such that arms 56 are compressed by sleeve 20, and more particularly by end 82 of sleeve 20, to capture bone fastener 150. Arms 56 are circumferentially disposed and equidistantly spaced apart.

Arms 56 are spaced apart by gaps 70 defined by opposite sidewalls 72, which may be planar sidewalls. Sleeve 20 engages tube 18 such that arms 56 converge to capture bone fastener 150 when compressed by sleeve 20, as described herein. Collet 60 includes an inner circumferential flange 62. Flange 62 is configured to facilitate capture of bone fastener 150. Flange 62 is configured to apply a force to an angled side of head 152, thereby pushing head 152 and causing bone fastener 150 to translate axially into cavity 54 and into engagement with drive 16. The subject side of the head 152 is angled in that it is not perpendicular to approaching flange 62, and such that a force at intersection of it and the flange 62 causes relative motion, such as causing one or both of flange 62 and surface to slide along the other.

In various embodiments, flange 62 engages the outer surface of the head 152 in the co-axial, capture orientation to provide for more than a point contact, and more than a linear contact, between the flange 62 and the outer surface of head 152. Rather, the contact includes significant surface-to-surface contact, such as some or fully flat- or planar-surface-to-surface contact, between flange 62 and fastener 150.

Sleeve 20 is disposed circumferentially about tube 18, as shown in FIG. 2. Sleeve 20 extends along axis X1 between an end 80 and an end 82. Sleeve 20 includes an inner surface 84 that defines a cavity, such as, for example, a passageway 86. Tube 18 is configured for moveable disposal within passageway 86.

As mentioned, in some embodiments, sleeve 20 includes an engagement surface, such as, for example, a threaded surface configured for engagement with a corresponding, e.g. threaded surface of tube 18. Engagement of the surfaces, such as threading of the threaded surfaces causes translation of outer sleeve 20 relative to tube 18.

The translation of outer sleeve 20 relative to tube 18 causes the collet 60 to secure, or secure more, around and against head 152 of bone fastener 150. In various embodiments, the arrangement is configured and used such that drive 16 is already engaged with head 152 when the colleting is performed. In various, contemplated, embodiments, the arrangement is configured and used such that the colleting creates engagement or substantiates, or increases, the act of engaging head 15.

In some embodiments, sleeve 20 includes a cylindrical configuration, making for a circular cross-section configuration. In some embodiments, the cross-section of sleeve 20 may have various configurations, for example, oval, rectangular, polygonal, irregular, tapered, offset, staggered, uniform and non-uniform. In some embodiments, one or all of the surfaces of sleeve 20 may have any of various surface configurations, such as, for example, smooth, rough, threaded for connection with surgical instruments, arcuate, undulating, porous, semi-porous, dimpled, polished and/or textured.

Figure 5:
FIG. 5 is a side view of components of one embodiment of a surgical system in accordance with the principles of the present disclosure.
Figure 7:
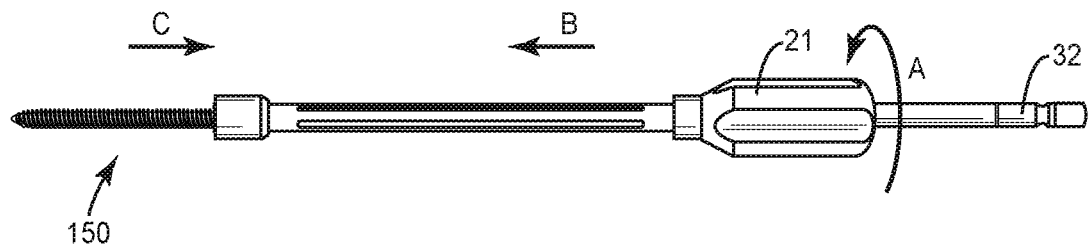
FIG. 7 is a side view of the components shown in FIG. 6.

Sleeve 20 is mounted with tube 18 for axial translation relative to tube 18 and arms 56 thereof. Sleeve 20 is translatable relative to tube 18 to move arms 56, as described herein, between the open orientation, as shown in FIG. 5, and the capture orientation, as shown in FIG. 7. Arms 56 are initially resiliently biased outwardly and/or in an expanded configuration such that arms 56 are in the open orientation in which arms 56 are spaced apart. As sleeve 20 axially translates, arms 56 are compressed or contracted inwardly. The engagement of sleeve 20 with tube 18 and the corresponding force applied thereto moves arms 56 to the capture orientation to engage bone fastener 150. Arms 56 pull and/or draw head 152 along axis X1 into cavity 54 for capture of bone fastener 150. In some embodiments, sleeve 20 includes a protrusion, such as, for example, depth stop 90. Stop 90 is configured to provide indication, for a working physician, of a depth of surgical instrument 12 relative to a patient body.

For example, in use, surgical instrument 12 is disposed in the open orientation such that sleeve 20 is disengaged from collet 60, as shown in FIG. 5. Collet 60 is disposed in an open orientation, as described herein, such that arms 56 are expanded and spaced apart. In some embodiments, head 152 includes an outer surface having planar surfaces or flats and/or arcuate surfaces. In some embodiments, the planar surfaces of head 152 are aligned with laser markings disposed with drive 16. Engagement portion 36 is aligned with socket 158. As head 152 is translated into cavity 54, head 152 pushes against arms 56, causing arms 56 to expand around head 152 to provisionally capture bone fastener 150.

In various embodiments, sleeve 20 includes a gripping portion 21. In some embodiments, portion 21 includes a surface, such as, for example, a knurled surface configured to facilitate gripping of sleeve 20. Portion 21 is rotated, for example, in a clockwise direction, as shown by arrow A in FIG. 7.

In various embodiments, drive 16 and sleeve 20 have corresponding threads 23. While, for clarity, threads are shown expressly on the driver, including, by dashed lines, beneath the gripping portion 21 of the sleeve 20, presentation of the threads 23 is considered to show both of the engaging threads, of drive 16 and sleeve 20.

For creating relative motion between the drive 16 and sleeve 20, a user can hold tube 20, or gripping portion 21 that is part of or connected rigidly to tube 20, and can hold drive 16, or a selected conventional handle (not shown) connected removably and rigidly to drive 16. Rotation of sleeve 20 causes sleeve 20 to axially translate with respect to drive 16. The translation also causes sleeve 20 to translate axially along tube 18, in the direction shown by arrow B in FIG. 7, to collapse collet 60 and compress arms 56 to capture bone fastener 150, as described herein. Compression of arms 56 causes flange 62 to apply a force to head 152. Flange 62 pulls and/or draws bone fastener 150 axially into cavity 54, or further or more robustly into cavity 54, in a direction shown by arrow C in FIG. 7, to facilitate or substantiate disposal of engagement portion 36 with socket 158. As bone fastener 150 translates into cavity 54, shoulder 49 engages, or further engages, surface 164 to deform and/or compress surface 164 to form a rigid, coaxial connection between surgical instrument 12 and bone fastener 150.

Engagement portion 36 of drive 16 is disposed with socket 158, as described herein, such that surgical instrument 12 is engaged with bone fastener 150 in a rigid, coaxial connection to manipulate, drive, torque or insert bone fastener 150 for treatment of tissue, as described herein. To release surgical instrument 12 from bone fastener 150, portion 21 is rotated, for example, in a counter-clockwise direction, as shown by arrow D in FIG. 8.

Figure 8:
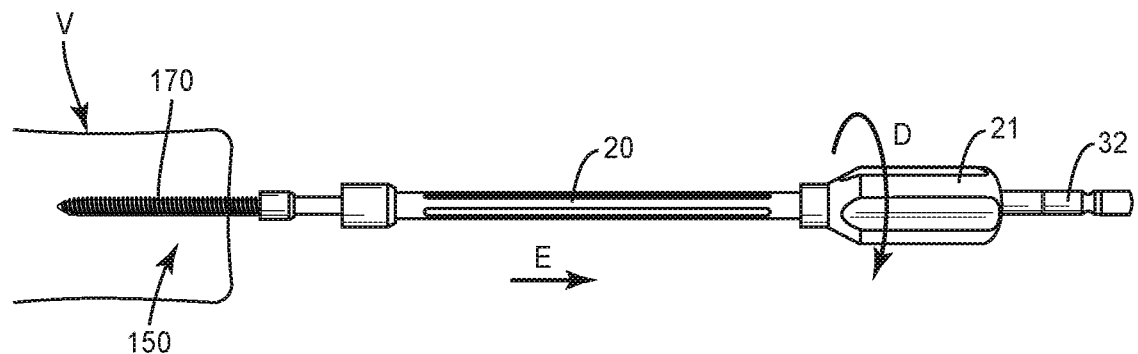
FIG. 8 is a side view of the components shown in FIG. 6 disposed with vertebrae.
Figure 9:
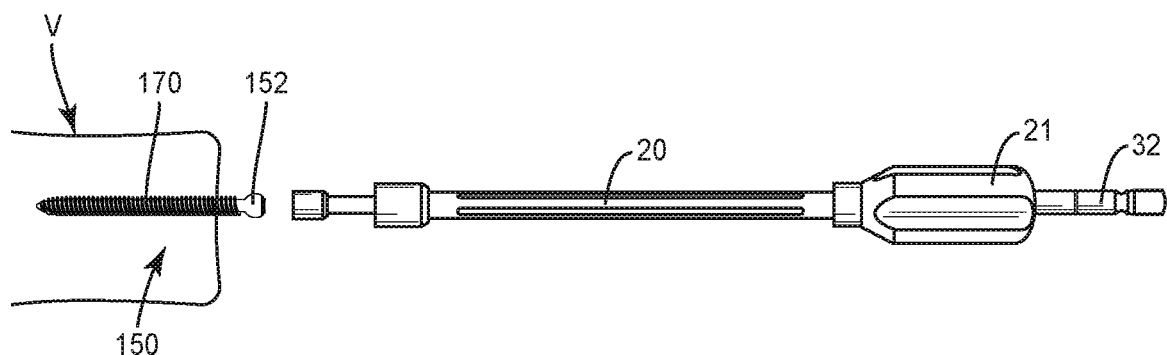
FIG. 9 is a side view of the components shown in FIG. 6 disposed with vertebrae.
Figure 10:
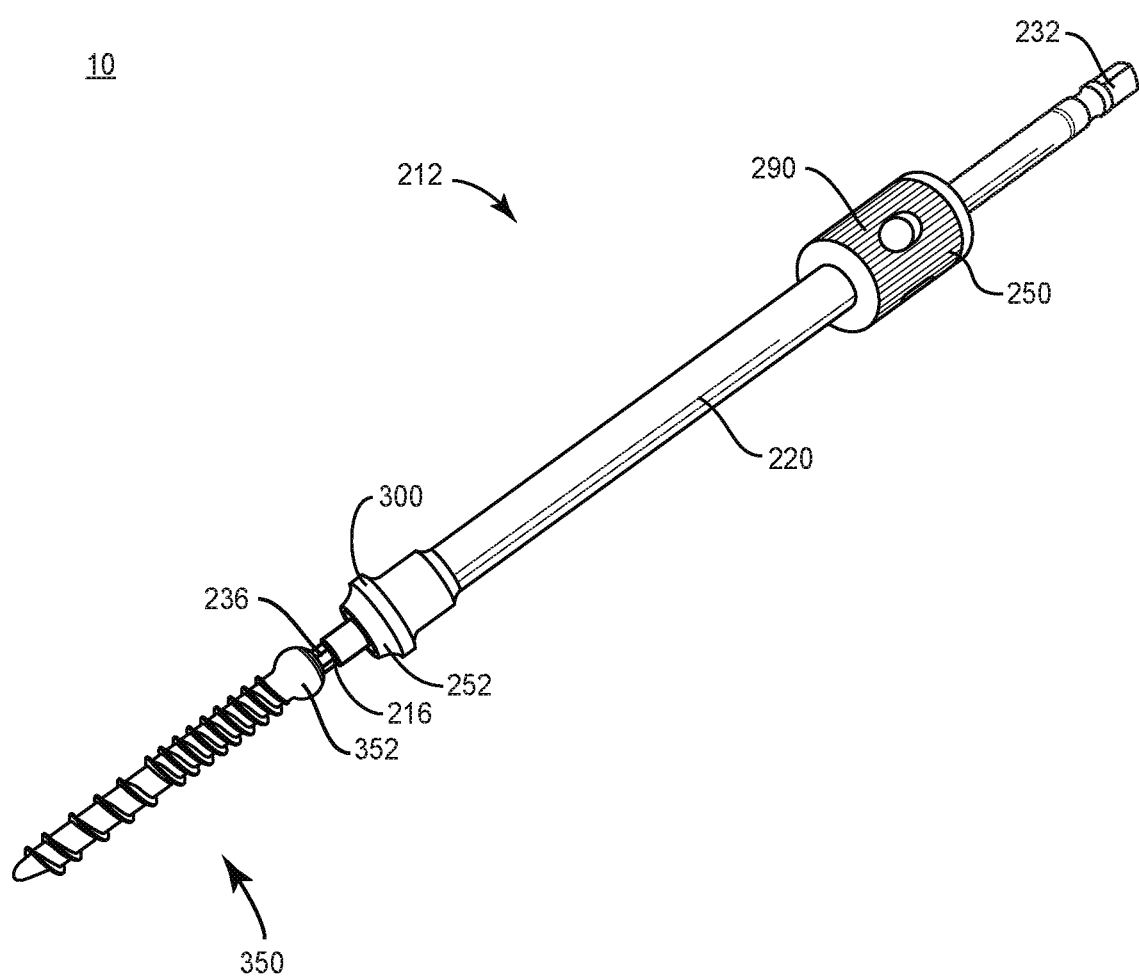
FIG. 10 is a perspective view of components of one embodiment of a surgical system in accordance with the principles of the present disclosure.

Due to thread formation, rotation of sleeve 20 causes sleeve 20 to axially translate along tube 18, in the direction shown by arrow E in FIG. 8, to axially translate and disengage from collet 60 allowing arms 56 to expand. Surgical instrument 12 is disengageable from bone fastener 150, as shown in FIG. 9.

Bone fastener 150 includes head 152. Head 152 includes a surface 154 that defines a drive interface, such as, for example, socket 158. Socket 158 is configured for a mating engagement with engagement portion 36. Surface 154 defines a hexalobe configuration, or other suitably shaped configuration. Surface 154 defines a plurality of protrusions 160 having elliptical edges 162 configured for engagement with lobes 40. In some embodiments, socket 158 includes six (6) protrusions 160. Protrusions 160 are spaced apart and disposed circumferentially about engagement portion 36.

Figure 4:
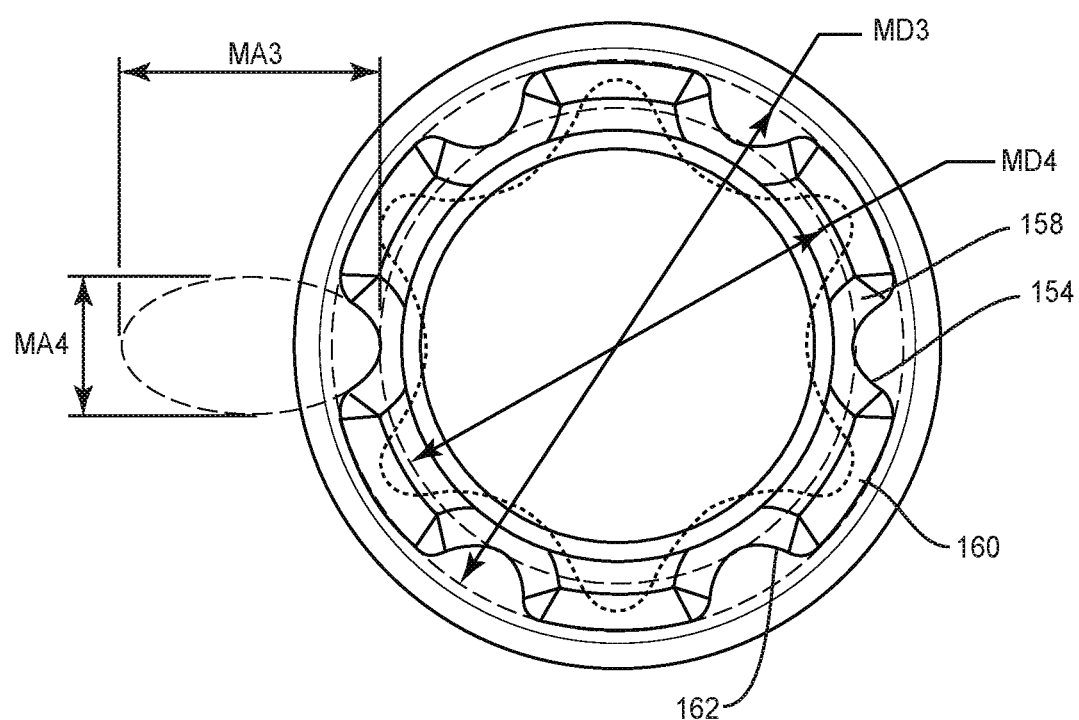
FIG. 4 is an end view of components of one embodiment of a surgical system in accordance with the principles of the present disclosure.

Edge 162 is defined by an ellipse having a major axis MA3 and a minor axis MA4, as shown in FIG. 4. In some embodiments, major axis MA3 is approximately 2.1 mm. In some embodiments minor axis MA4 is approximately 1.15 mm. Socket 158 includes a depth D1 dimensioned to receive engagement portion 36. In some embodiments, depth D1 is equal to length L1. Socket 158 includes a major diameter MD3 and a minor diameter MD4, as shown in FIG. 4. In some embodiments, major diameter MD3 is approximately 4.6 mm. In some embodiments, minor diameter MD4 is approximately 3.8 mm. Engagement of lobe 40 with socket 158 is configured to maximize torque transmission between drive 16 and bone fastener 150. In some embodiments, the configuration of lobes 40 with socket 158 is configured to resist and/or prevent stripping of socket 158 during rotation.

Head 152 includes surface 164. In some embodiments, surface 164 includes a countersunk configuration disposed about an opening of socket 158. As flange 62 applies a force to head 152 causing bone fastener 150 to translate axially into cavity 54, shoulder 49 engages surface 164 to deform and/or compress surface 164 to form the rigid connection between surgical instrument 12 and bone fastener 150. Engagement of lobe 40 with socket 158 is configured to maximize torque transmission between drive 16 and bone fastener 150. In some embodiments, the configuration of lobes 40 with socket 158 is configured to resist and/or prevent stripping of socket 158 during rotation.

As mentioned, one of the prevailing benefits of socket 158 and drive 16 of the present technology is that much more surface-to-surface contact is created between the drive 16 and socket 158 in use of the present technology as compared to prior drive/socket arrangements. This configuration resists and/or prevents slipping, and allows for creation of greater torque in driving bone fastener 150.

Figure 6:
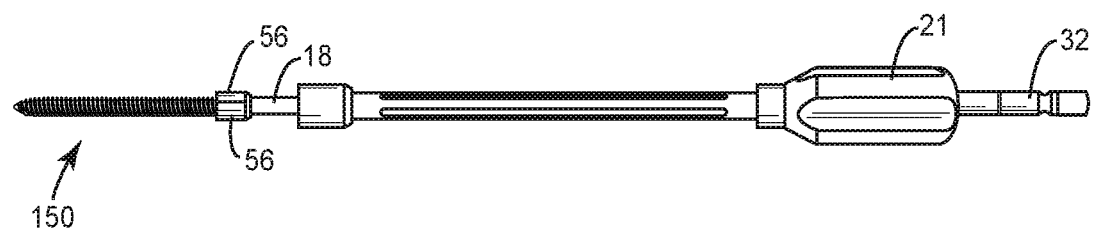
FIG. 6 is a side view of components of one embodiment of a surgical system in accordance with the principles of the present disclosure.

Bone fastener 150 includes a shaft 170 (FIG. 2) configured for penetrating tissue. In various embodiments, at least a portion of shaft 170 has a generally cylindrical shape, and thus a generally circular cross-sectional configuration. Shaft 170 may also taper, such as by narrowing in width approaching a tip of the shaft. Shaft 170 includes an outer surface having an external thread form, as shown in FIGS. 6 et. seq. In some embodiments, the external thread form may include a single thread or a plurality of discrete threads. In some embodiments, other engaging structures may be located on shaft 170, such as, for example, a nail configuration, barbs, expanding elements, raised elements and/or spikes to facilitate engagement of shaft 170 with tissue.

In some embodiments, all or at least a portion of shaft 170 has any of various cross-sectional configurations, such as, for example, oval, oblong, triangular, square, polygonal, irregular, uniform, non-uniform, offset, staggered, undulating, arcuate, variable and/or tapered. In some embodiments, the outer surface of shaft 170 may include one or a plurality of openings. In some embodiments, all or only a portion of the outer surface of shaft 170 may have any of various surface configurations to enhance fixation with tissue, such as, for example, rough, arcuate, undulating, mesh, porous, semi-porous, dimpled and/or textured. In some embodiments, all or only a portion of shaft 170 may be disposed at alternate orientations, relative to its longitudinal axis, such as, for example, transverse, perpendicular and/or other angular orientations such as acute or obtuse, co-axial and/or may be offset or staggered. In some embodiments, all or only a portion of shaft 170 may be cannulated.

In assembly, operation and use, surgical system 10, is employed with a surgical procedure, such as, for example, a surgical treatment of an applicable condition or injury of an affected section of a spinal column and adjacent areas within a body. In some embodiments, surgical system 10 can be used in any surgical method or technique including open surgery, mini-open surgery, minimally invasive surgery and percutaneous surgical implantation, whereby vertebrae V is accessed, such as through a mini-incision, and possibly also via a sleeve (not shown) that provides a protected passageway to vertebrae V. Once access to the surgical site is obtained, the particular surgical procedure can be performed for treating the spine disorder.

An incision is made in the body of a patient and a cutting instrument (not shown) creates a surgical pathway. A preparation instrument (not shown) can be employed to prepare tissue surfaces of or surrounding vertebrae V, as well as for aspiration and irrigation of a surgical region.

Surgical instrument 12 is disposed in an open orientation, as described herein and shown in FIG. 5, such that sleeve 20 is disengaged from collet 60. Collet 60 is disposed in the open orientation such that arms 56 are expanded and spaced apart. For embodiments having laser or other markings or indicia, corresponding marks or indicia of head 152 and of instrument 12, such as of the collet or drive, are aligned. Alignment can be performed to orient planar surfaces of the head with the drive as desired, for instance, as described above regarding uni-axial bone fasteners. In various embodiments the alignment includes actually aligning all or a portion or edge of one or both of planar surfaces of head 152 with one or more laser markings disposed with drive 16 and/or aligning marking or indicia of head 152 with marking or indicia of sleeve 20. Engagement portion 36 is aligned with socket 158, Head 152 is translated into cavity 54 such that arms 56 expand to provisionally capture bone fastener 150.

Portion 21, or at least sleeve 20, is rotated, for example, in a clockwise direction, as shown by arrow A in FIG. 7, with respect to tube 18. Based on relative threading between tube 18 and sleeve 20, rotation of sleeve 20 causes sleeve 20 to axially translate along tube 18, in the direction shown by arrow B in FIG. 7. With the translation, as end 82 contacts arms 56, already holding head 152, arms 56 are caused to collapse, forming collet 60. The action thus collapses collet 60 and compresses arms 56 to capture, or further or more robustly capture, bone fastener 150, as described herein.

Compression of arms 56 causes flange 62 to apply a force to head 152. Flange 62 pulls and/or draws bone fastener 150 axially into cavity 54, or at least further into cavity 54, in a direction shown by arrow C in FIG. 7, to facilitate or substantiate disposal of engagement portion 36 with socket 158. As bone fastener 150 translates into, or further into, cavity 54, shoulder 49 of drive 16 engages or further engages surface 164 of heard 152 to deform and/or compress surface 164 to form a rigid, or more rigid, coaxial connection between surgical instrument 12 and bone fastener 150.

Engagement portion 36 is disposed with socket 158, as described herein, such that surgical instrument 12 can be manipulated to drive, torque, insert or otherwise connect bone fastener 150 with vertebrae V, as shown in FIG. 8. To release surgical instrument 12 from bone fastener 150, portion 21 is rotated, for example, in a counter-clockwise direction, as shown by arrow D in FIG. 8. Rotation of sleeve 20 causes sleeve 20 to axially translate along tube 18, in the direction shown by arrow E in FIG. 8, to axially translate and disengage from collet 60 allowing arms 56 to expand. Surgical instrument 12 is disengageable from bone fastener 150, as shown in FIG. 9, with bone fastener 150 fixed with vertebrae V.

Upon completion of a procedure, surgical instrument 12, additional surgical instruments and/or tools, assemblies and non-implanted components of surgical system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10.

In some embodiments, surgical system 10 may include one or a plurality of plates, connectors and/or bone fasteners for use with a single vertebral level or a plurality of vertebral levels. In some embodiments, one or more of bone fasteners may be engaged with tissue in various orientations, such as, for example, series, parallel, offset, staggered and/or alternate vertebral levels. In some embodiments, one or more bone fasteners may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

In various embodiments, as shown in FIGS. 10-17, surgical system 10, includes a surgical instrument 212, similar to surgical instrument 12 described herein, configured for use with a bone fastener 350, similar to bone fastener 150 described herein. Surgical instrument 212 includes an inner drive 216, similar to inner drive 16 described herein, engageable with a head 352 of bone fastener 350 and an outer sleeve 220, similar to outer sleeve 20 described herein, movable relative to drive 216 to dispose drive 216 in a co-axial, capture orientation to facilitate accurate engagement of bone fastener 350 with tissue.

Figure 11:
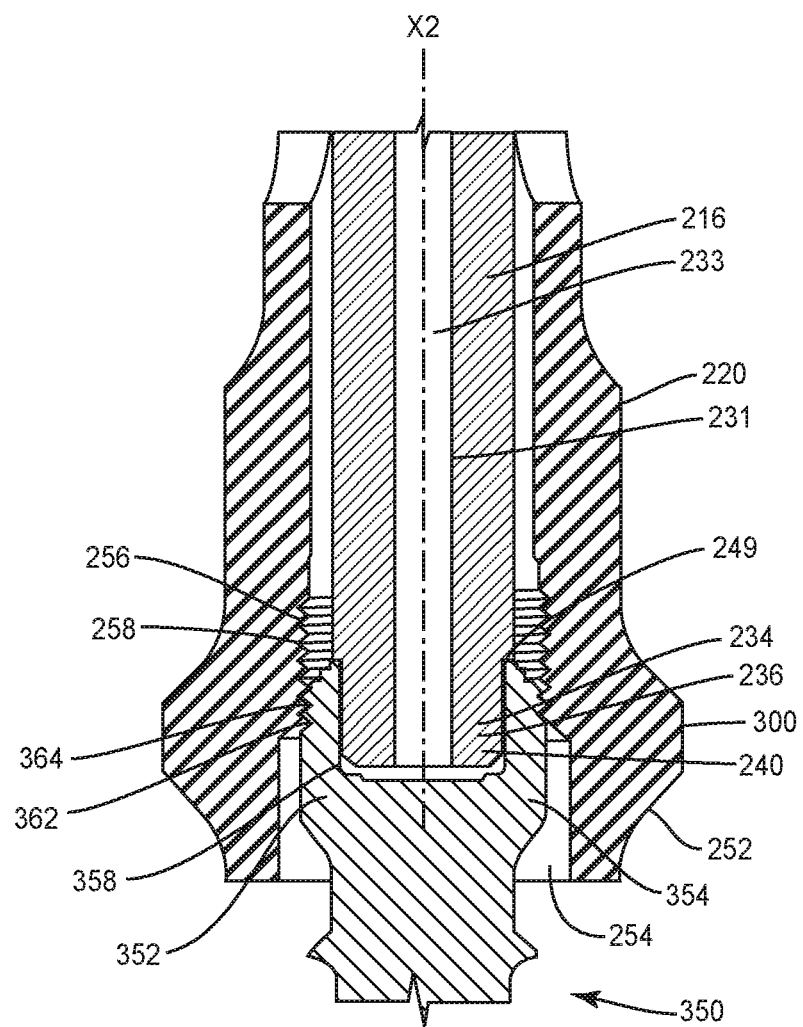
FIG. 11 is an enlarged cross section view of components of one embodiment of a surgical system in accordance with the principles of the present disclosure.

Drive 216 includes a shaft 230 that extends between an end 232 and an end 234. Drive 216 extends along an axis X2, as shown in FIG. 11. In some embodiments, end 232 includes a hexagonal geometry configured for engagement with a similarly shaped surgical tool, such as, for example, a portion of a driver (not shown). Shaft 230 includes a surface 231 that defines a passageway 233 such that shaft 230 includes a cannulated configuration.

Figure 12:
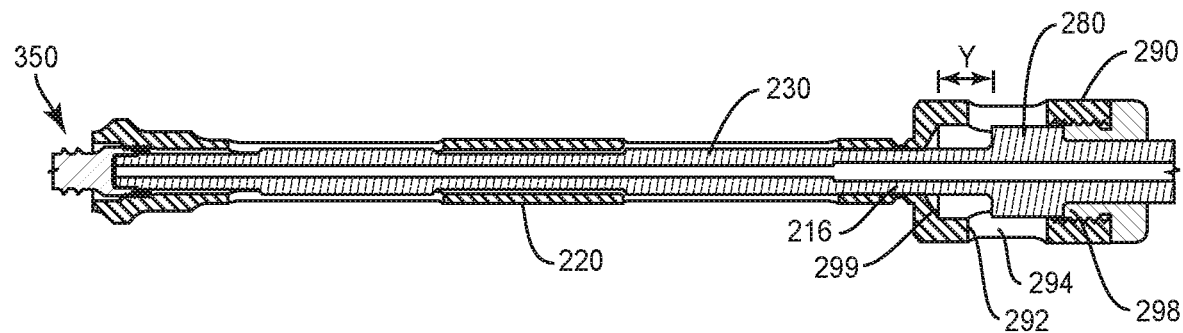
FIG. 12 is a cross section view of components of one embodiment of a surgical system in accordance with the principles of the present disclosure.

Shaft 230 includes a circumferential flange 280. Flange 280 is configured for disposal with a portion of sleeve 220, as described herein. Shaft 230 is translatable relative to sleeve 220 and bone fastener 350 to facilitate engagement with bone fastener 350, as described herein. Shaft 230 is translatable a distance Y along axis X2 relative to sleeve 220, as shown in FIG. 12. Translation of shaft 230 facilitates engagement of an engagement portion 236, similar to engagement portion 36 described herein, of drive 216 with bone fastener 350 prior to engagement of sleeve 220 with bone fastener 150, as described herein. This configuration facilitates engagement of drive 216 prior to run out of a threaded engagement between sleeve 220 and bone fastener 350, as described herein.

End 234 includes a drive interface, such as, for example, engagement portion 236, which is configured to mate with a socket 358, similar to socket 158 described herein, of head 352, as shown in FIG. 11. Engagement portion 236 includes an outer surface 238 that defines lobes 240 disposed circumferentially about engagement portion 236, similar to lobes 40 as described herein. Engagement portion 236 includes a protrusion, such as, for example, a shoulder 249, as shown in FIG. 11. Shoulder 249 is circumferentially disposed about inner drive 216, similar to shoulder 49 as described herein. In some embodiments, engagement portion 236 includes visual indicia. In some embodiments, the visual indicia includes a laser marking configured to facilitate indexing engagement portion 236 with socket 358, as described herein.

Sleeve 220 extends between an end 250 and an end 252. In some embodiments, sleeve 220 may have various cross-section configurations, such as, for example, oval, oblong, triangular, rectangular, square, polygonal, irregular, uniform, non-uniform, variable, tubular and/or tapered. In various embodiments, end 250 includes gripping portion 290. In some embodiments, portion 290 includes a surface, such as, for example, a knurled surface configured to facilitate gripping of sleeve 220 for rotation, as described herein.

End 252 is disposed in a spaced apart relation with end 234 of drive 216 to define a cavity 254, as shown in FIG. 11. Cavity 254 is configured for disposal of head 352. End 252 includes a surface 256 that defines a threaded portion 258. Portion 258 is configured for engagement with a portion of bone fastener 350 to pull and/or draw bone fastener 350 axially into cavity 254 and into engagement with drive 216, as described herein.

Figure 13:
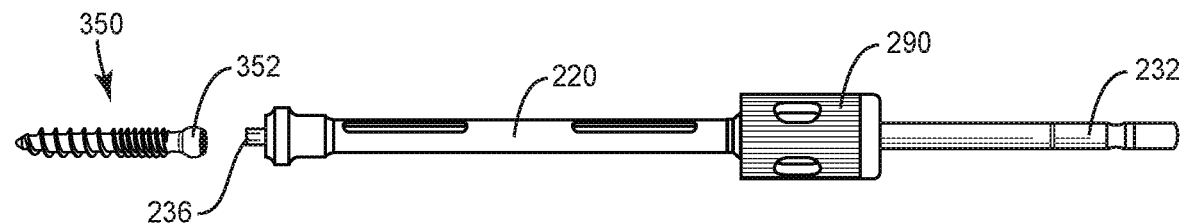
FIG. 13 is a side view of components of one embodiment of a surgical system in accordance with the principles of the present disclosure.
Figure 14:
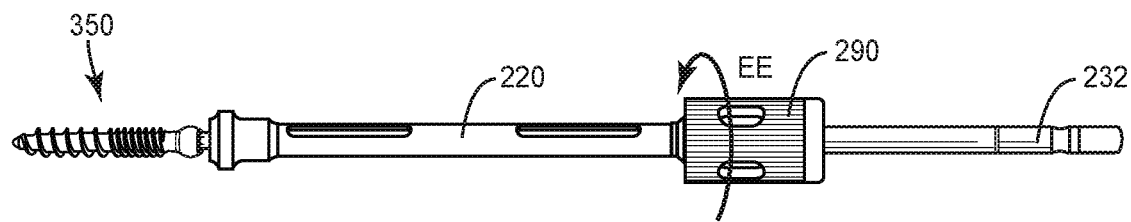
FIG. 14 is a side view of the components shown in FIG. 13.
Figure 15:
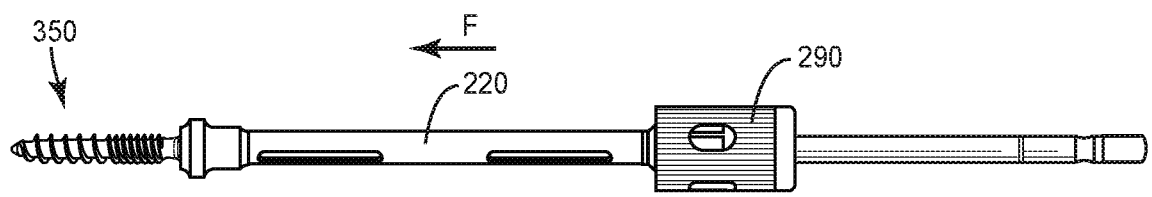
FIG. 15 is a side view of the components shown in FIG. 13.

Portion 290 includes at least one surface 292 that defines a barrel 294. Barrel 294 is configured for moveable disposal of a flange 280 of shaft 230. Portion 290 includes a proximal limit 298 and a distal limit 299 of axial translation of drive 216 relative to sleeve 220, as shown in FIG. 12. Flange 280 is translatable a distance Y within barrel 294 between limits 298, 299. Flange 280 is distally translatable to limit 299 so that engagement portion 236 extends past end 252 to facilitate engagement with bone fastener 350, as shown in FIG. 13. Engagement portion 236 is connected with bone fastener 350 and sleeve 220 is threaded with bone fastener 350, as described herein, such that flange 280 is proximally translatable to limit 298. Limit 298 resists and/or prevents drive 216 from further proximal translation by engagement of flange 280 with limit 298 and/or run out of the threaded engagement between sleeve 220 and bone fastener 350, as described herein.

Sleeve 220 is mounted with drive 216 for axial translation relative to drive 216. Sleeve 220 is translatable relative to drive 216 to capture bone fastener 350 with surgical instrument 212. Sleeve 220 pulls and/or draws head 352 along axis X2 into cavity 254 for capture of bone fastener 350. End 252 includes a protrusion, such as, for example, depth stop 300. Stop 300 is configured to provide indication of a depth of surgical instrument 212 relative to a patient body.

Bone fastener 350 includes head 352. Head 352 includes a surface 354 that defines a drive interface, such as, for example, socket 358. Socket 358 is configured for a mating engagement with engagement portion 236, as described herein. Surface 354 defines a hexalobe configuration, as an example. Surface 354 defines a plurality of protrusions having elliptical edges, similar to the protrusions and edges of surface 154 described herein, configured for engagement with lobes 240. Head 352 includes surface 362. Surface 362 defines a threaded portion 364 configured for engagement with portion 258. The threaded engagement of portions 364, 258 causes sleeve 220 to pull and/or draw bone fastener 350 axially into cavity 254 and into engagement with drive 216 to form a rigid, co-axial connection between surgical instrument 212 and bone fastener 350. Bone fastener 350 includes a shaft 370 configured for penetrating tissue, similar to shaft 170, as described herein.

Figure 16:
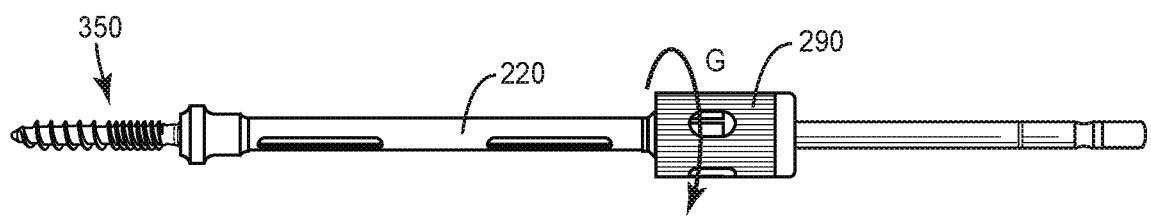
FIG. 16 is a side view of the components shown in FIG. 13.
Figure 17:
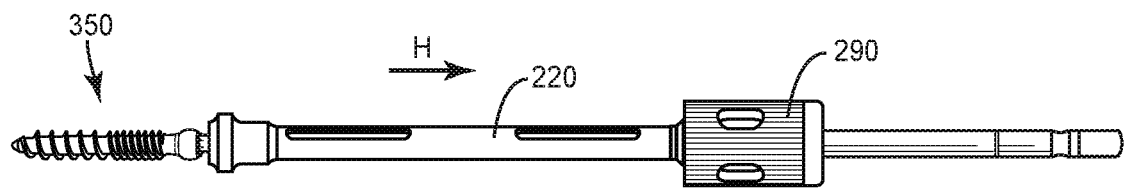
FIG. 17 is a side view of the components shown in FIG. 13.

For example, in use, similar to the systems and methods described with regard to surgical instrument 12, surgical instrument 212 is disposed in an open orientation, as shown in FIG. 13, such that engagement portion 236 extends from end 252, as described herein. Engagement portion 236 is aligned with socket 358. Head 352 is translated into cavity 254. Portion 364 threadingly engages portion 258. Sleeve 220 is rotated, for example, in a clockwise direction, as shown by arrow EE in FIG. 14, relative to drive 216. Sleeve 220 axially translates, in the direction shown by arrow F in FIG. 15, relative to drive 216. Portion 364 threadingly engages portion 258 to pull and/or draw bone fastener 350 axially into cavity 254 and into engagement with drive 216 to form a rigid, co-axial connection between surgical instrument 212 and bone fastener 350, as shown in FIG. 16.

Engagement portion 236 is disposed with socket 358, as described herein, such that surgical instrument 212 is engaged with bone fastener 350 in a rigid, coaxial connection to manipulate, drive, torque or insert bone fastener 350 for treatment of tissue, similar to that described herein. To release surgical instrument 212 from bone fastener 350, sleeve 220 is rotated relative to drive 216, for example, in a counter-clockwise direction, as shown by arrow G in FIG. 16. Rotation of sleeve 220 causes portion 364 of head 350 to threadingly disengage from portion 258 of end 252 of sleeve 220, such that sleeve 220 axially translates relative to drive 216 and bone fastener 350, in the direction shown by arrow H in FIG. 17. Surgical instrument 212 is disengageable from bone fastener 350.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a handle comprising opposite proximal and distal portions, the proximal portion comprising a plurality of spaced apart lobes, the lobes defining a gripping portion, the distal portion comprising a collar, the collar being fixed relative to the gripping portion;
   a first member including opposite proximal and distal ends, the first member extending through the handle such that the proximal end is positioned above the proximal portion and the distal end is positioned below the distal portion, the first member including a first element engageable with an inner surface of a head of a bone fastener and a second element engageable with an outer surface of the head, wherein the first member defines a first-member longitudinal axis and the bone fastener defines a bone-fastener longitudinal axis; and
   a second member fixed directly to the handle to permanently prevent movement of the second member relative to the handle, the second member defining a second-member longitudinal axis, and movable relative to the first member and engageable with the second element to dispose the first element and the second element with the head in a co-axial, capture orientation wherein the first-member, bone-fastener, and second-member longitudinal axes are aligned.

2. A surgical instrument as recited in claim 1, wherein the first element includes an inner drive and the second element includes an outer tube that define a cavity therebetween for disposal of the head.

3. A surgical instrument as recited in claim 1, wherein the second element is radially movable relative to the first element.

4. A surgical instrument as recited in claim 1, wherein the second element is biased radially outward relative to the first element to an open orientation.

5. A surgical instrument as recited in claim 1, wherein the first member comprises a collet that is expandable to receive the head and collapsible to dispose the first and second elements with the head in the co-axial, capture orientation.

6. A surgical instrument as recited in claim 1, wherein the second element includes an inner circumferential flange.

7. A surgical instrument as recited in claim 1, wherein the second element is configured to engage the outer surface to draw the inner surface into fixation, or greater fixation, with the first element in the co-axial, capture orientation.

8. A surgical instrument as recited in claim 1, wherein the second element is configured to engage the outer surface of the head in the co-axial, capture orientation to provide for more than a point contact, and more than a linear contact, between the second element and the outer surface of the head.

9. A surgical instrument as recited in claim 1, wherein the second member includes a tissue depth stop.

10. A surgical instrument as recited in claim 1, wherein the second member includes an outer sleeve and the first member includes a collet.

11. A surgical instrument as recited in claim 1, wherein the first member comprises a shoulder that, in operation of the instrument, contacts and deforms an exposed surface of the head of the bone fastener, to enhance engagement between the first member and the head.

12. A surgical instrument as recited in claim 1, wherein the handle defines a maximum diameter of the surgical instrument.

13. A surgical instrument as recited in claim 1, wherein the handle comprises a knurled surface configured to facilitate gripping.

14. A surgical instrument as recited in claim 1, wherein the handle is connected rigidly to the second member.

15. A surgical method comprising:
   providing the surgical instrument recited in claim 1;
   engaging the second member with the head, yielding a first engagement;
   engaging the outer surface of the head with an inner portion of an outer tube the first member, surrounding the second member, yielding a second engagement; and
   driving the bone fastener into patient tissue by force applied to the fastener via the second member, with alignment between longitudinal axes of the second member, the bone fastener, and the first member being maintained based on the first and second engagements.

16. A surgical method as recited in claim 15, wherein engaging the outer surface of the head of the bone fastener with the inner portion of the outer tube comprises engaging inner threads, of the inner portion of the outer tube, with outer threads, of the outer surface of the head of the bone fastener.

17. A surgical instrument comprising:
   a handle comprising opposite proximal and distal portions, the proximal portion including a plurality of spaced apart lobes defining a gripping portion, the distal portion defining a collar, the collar being fixed relative to the gripping portion;
   an inner drive including opposite proximal and distal ends, the inner drive extending through the handle such that the proximal end is positioned above the proximal portion and the distal end is positioned below the distal portion, the distal end being engageable with an inner surface of a head of a bone fastener, wherein the inner drive defines an inner-drive longitudinal axis and the bone fastener defines a bone-fastener longitudinal axis; and
   an outer sleeve fixed directly to the collar to permanently prevent movement of the outer sleeve relative to the handle, the outer sleeve having an outer-sleeve axis and including a threaded surface engageable with a threaded portion of an outer surface of the head to dispose the inner drive and the outer sleeve with the head in a co-axial, capture orientation, wherein the inner-drive longitudinal axes, the bone-fastener longitudinal axis, and the outer-sleeve axis are aligned.

18. A surgical instrument as recited in claim 17, wherein when the threaded surface of the outer sleeve is threaded with the threaded portion of the outer surface, the inner surface of the head is drawn into fixation, or into greater fixation, with the inner drive in the co-axial, capture orientation.

19. A surgical instrument as recited in claim 17, wherein the outer sleeve includes a barrel having a proximal limit and a distal limit limiting axial translation of the inner drive relative to the outer sleeve in operation of the surgical instrument, wherein the proximal limit is configured to resist and/or prevent thread runout of the outer sleeve and the outer surface.

20. A surgical instrument as recited in claim 17, wherein the outer sleeve includes a tissue depth stop.

* * * * *